US00PP17829P3

(12) United States Plant Patent

Falstad et al.

(10) Patent No.: US PP17,829 P3

(45) Date of Patent: Jun. 26, 2007

(54) *BRUNNERA MACROPHYLLA* PLANT NAMED 'LOOKING GLASS'

(50) Latin Name: *Brunnera macrophylla*
Varietal Denomination: Looking Glass

(75) Inventors: Clarence H. Falstad, Holland, MI (US); John D. Walters, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 866 days.

(21) Appl. No.: 10/724,961

(22) Filed: Dec. 1, 2003

(65) Prior Publication Data

US 2007/0089212 P1 Apr. 19, 2007

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP13,706 P3 4/2003 Hirsch et al.
PP13,859 P3 6/2003 Walters

FOREIGN PATENT DOCUMENTS

EP 9772 P 3/2003

*Primary Examiner*—Kent Bell

(57) ABSTRACT

The new and distinctive cultivar of *Brunnera* named 'Looking Glass' with light blue flowers in the spring and characterized by an intense silver coating on top of the leaves, suitable for specimen or mass landscape usage, or potted culture.

2 Drawing Sheets

Botanical classification: *Brunnera macrophylla* (Adams) I. M. Johnston.
Variety denomination: 'Looking Glass'.

SUMMARY, BACKGROUND AND ORIGIN OF THE PLANT

The new and distinct *Brunnera macrophylla* 'Looking Glass', hereinafter also referred to as 'Looking Glass' and 'the Plant,' is a new and unique sport of the cultivar *Brunnera macrophylla* 'Jack Frost' U.S. Plant Pat. No. 13,859. The Plant has been asexually propagated by careful tissue culture propagation of the shoot tips, at the same nursery in Zeeland, Mich. Tissue culture has produced plants identical to the originally discovered sport, and maintains those unique characteristics in subsequent generations.

*Brunnera macrophylla* (Adams) Johnst. is a hardy, herbaceous, sub-alpine perennial native to eastern Asia, western Caucasus and Mediterranean Europe. It has many common names, among them: Alkanet, Siberian Bugloss, and Forget-me-not.

*Brunnera* 'Looking Glass' was discovered as a single, non-induced sport in a batch of tissue culture propagated plants of *Brunnera* 'Jack Frost' in the fall of 2000 at a nursery in Zeeland, Mich. The Plant was grown to maturity and evaluated regularly at the same nursery. Two years later the Plant was propagated in test tubes using normal shoot tip tissue culture techniques at the nursery in Zeeland, Mich. Root initiation from shoots occurs in two to three weeks. Crops finish off at 15 cm tall and 20 cm wide in 3" containers in about five months of greenhouse conditions, and maintain their unique characteristics. The Plant flowers naturally in the spring following receipt of short days and long nights from fall growth.

BRIEF DESCRIPTION OF THE PLANT

*Brunnera macrophylla* 'Looking Glass' is very similar to 'Jack Frost' in habit, size and flowering. The major difference is the intensity of silver, and the amount of silver on the surface of the leaf. The leaves of 'Looking Glass' are almost uniform silver in color with just a thin line of green at the major veins and around the very margin of the leaves.

COMPARISON TO SIMILAR VARIETIES

*Brunnera macrophylla* 'Looking Glass' is a sport of *Brunnera macrophylla* 'Jack Frost' U.S. Plant Pat. No. 13,859, and is unique as a result of the amount of silver on the leaves. 'Looking Glass' is almost all silver on mature plants whereas the cultivar 'Jack Frost' has wider green veins and broader green margins. Other selections of *Brunnera macrophylla* include: a white margined cultivar named 'Variegata' (not patented), or also sometimes called 'Dawson's White' (not patented); a creamy yellow margined type named 'Hadspen Cream' (not patented) discovered by Eric Smith of England; 'Langtrees' (not patented), which has some silver barring on the leaves in a chevron pattern; 'Silver Wings' U.S. Plant Pat. No. 13,706, with a small coating of silver and a very thin creamy white chimeral margin on the leaves. There are also some white flowered forms called 'Betsy Baring' (not patented), 'Betty Bowring' (not patented) and 'Marley's White' (not patented), and a new cultivar with normal green leaves and white and blue striped flowers named 'Stars and Stripes' (not patented).

BRIEF DESCRIPTION OF THE DRAWINGS

The photographs of the new invention demonstrate the overall appearance of the plant including the unique traits. The colors are as accurate as reasonably possible with color reproductions. Light source and direction may cause the appearance of slight variation in brightness, saturation and hue.

DETAILED DESCRIPTION OF THE PLANT

Figure 1:
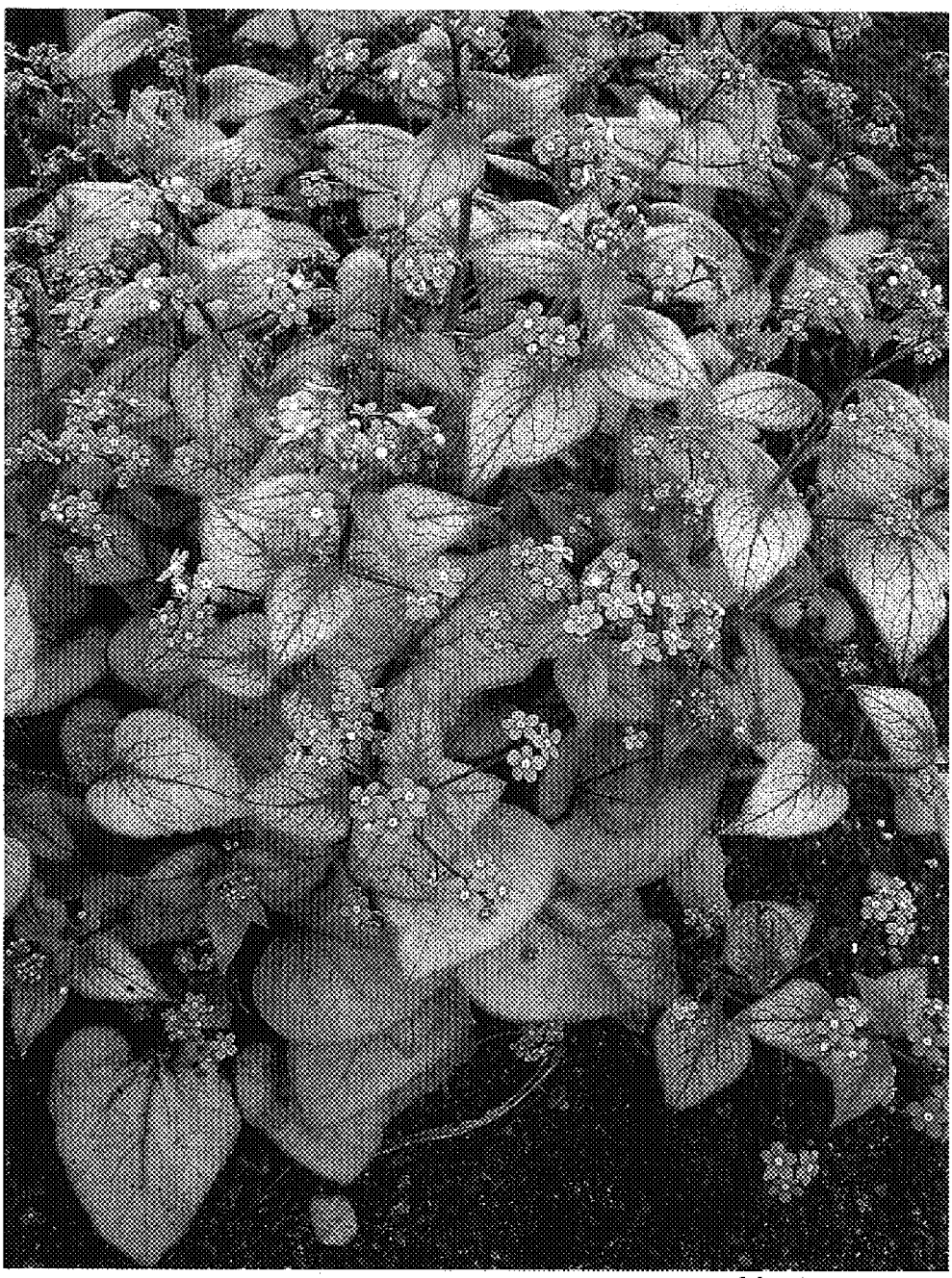
FIG. 1 shows the plant in flower in mid spring.
Figure 2:
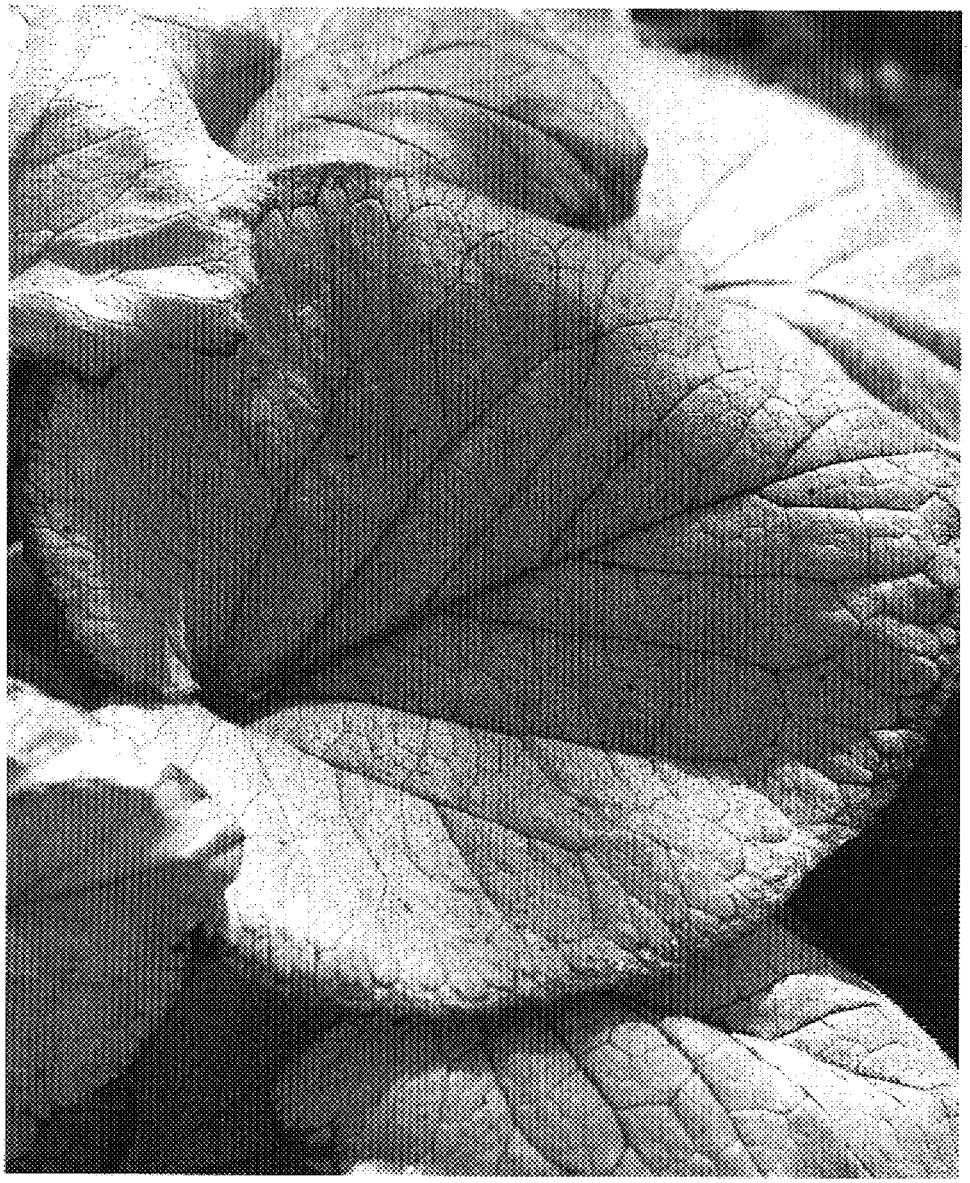
FIG. 2 shows a close-up of a few mature leaves in mid summer with the unique variegation.

The following descriptions with generic dictionary color usage are of a three-year-old plant growing in Zeeland, Mich. For more precise color descriptions the 2001 edition of The Royal Horticultural Colour Chart and the corresponding color references are used. The Plant has not been evaluated in all possible growing environments. The phenotype may vary slightly with different conditions such as fertility, light, moisture and temperature, however the genotype remains stable.

Plant habit: Foliage reaches heights of 45 cm and 50 to 70 cm wide. The leaves are cordate to reniform, coarsely pubescent, with long thin petioles basally attached to underground rhizomes. Plant shape is a domed mound.

Leaves: Entire; shape — cordate; apex — broadly acute; base — cordate; blade flat with no normal undulations although some are slightly convex, turning down around the edges in some conditions; finely pubescent on both surfaces; 12 to 15 cm long and 12 to 15 cm in width; base leaf color is a rich green — on the adaxial surface nearest RHS 137 A at the 2 mm wide major veins and the edge 2 to 3 mm of the leaf; abaxial leaf side between RHS 143 A and 142 B. The silver white coating is lighter than RHS 192 D or 190 D.

Petioles: Pubescent, 3 mm wide and up to 30 cm long; RHS 142 B.

Flowers: 120 to 180 individual flowers on paniculate cymes having smaller ovate cauline leaves either sessile or with short petioles, up to 60 cm tall and branches to 30 cm wide, remain in flower for three weeks, each flower persists up to one week; forming five lobed corolla, 7 mm diameter.

Petals: Adaxial side light blue, between RHS 106 A and RHS 106 B, deeper on younger flowers, with a short white corolla throat, abaxial side, or back of the flower about 108 D.

Peduncles: Pubescent, erect to 60 cm; to 4 mm diameter; green, RHS 138 B.

Flower bus: Globose, 1 to 2 mm diameter; RHS 76 C about four days prior to opening.

Sepals: Five, entire, narrowly acuminate, 1 mm long, less than 0.5 mm across, fused at base; green RHS 142 B on both surfaces.

Flower timing: Identical to *Brunnera macrophylla,* late April to May, in Zeeland, Mich.

Seeds and all the sexual organs: Identical to the species; single gynoecium 3 mm long, about RHS 193 D; androecium, 5; stamens white, about 2 to 3 mm long; anthers about 1 mm long and dark purple, RHS N 187 A; seeds small nutlet, less than 1 mm in diameter, dark brown to near black.

The Plant is hardy to USDA zone 3, tolerates late spring frosts, and persists after fall frosts. It has no serious pests. 'Looking Glass' performs well in shade, or sunny garden locations with some protection from the hottest sun. It grows best with an ample amount of moisture, but can tolerate drier gardens. It is also well suited for growing in containers, and is less prone to leaf scorch than 'Variegata'. 'Looking Glass' is useful as a potted plant, cut flower or in the landscape as a specimen plant or in mass.

I claim:

1. A new and distinct perennial *Brunnera macrophylla* plant named 'Looking Glass' as herein described and illustrated.

* * * * *